(12) United States Patent
Palena et al.

(10) Patent No.: US 10,080,526 B2
(45) Date of Patent: Sep. 25, 2018

(54) THREE DIMENSIONAL MICROFLUIDIC MULTIPLEXED DIAGNOSTIC SYSTEM

(75) Inventors: Patricia D. Palena, Plainsboro, NJ (US); Madiha Jafri, Mount Laurel, NJ (US); Jason Poleski, Moorestown, NJ (US); Sanipa K. Arnold, Huntingdon Valley, PA (US)

(73) Assignee: LEIDOS INNOVATIONS TECHNOLOGY, INC., Gaithersburg, MD (US)

( * ) Notice: Subject to any disclaimer, the term of this patent is extended or adjusted under 35 U.S.C. 154(b) by 1117 days.

(21) Appl. No.: 13/549,198

(22) Filed: Jul. 13, 2012

(65) Prior Publication Data

US 2013/0018243 A1 Jan. 17, 2013

Related U.S. Application Data

(60) Provisional application No. 61/507,412, filed on Jul. 13, 2011.

(51) Int. Cl.
| | |
|---|---|
| *A61B 5/05* | (2006.01) |
| *A61B 5/00* | (2006.01) |
| *A61B 5/053* | (2006.01) |
| *A61B 5/1473* | (2006.01) |
| *B01L 3/00* | (2006.01) |
| *B82Y 15/00* | (2011.01) |

(Continued)

(52) U.S. Cl.
CPC .......... *A61B 5/6847* (2013.01); *A61B 5/0538* (2013.01); *A61B 5/14735* (2013.01); *B01L 3/502753* (2013.01); *B82Y 10/00* (2013.01); *B82Y 15/00* (2013.01); *A61B 5/6865* (2013.01); *A61B 2560/0285* (2013.01); *A61B 2560/045* (2013.01); *A61B 2560/0443* (2013.01); *A61B 2562/028* (2013.01);
(Continued)

(58) Field of Classification Search
CPC . A61B 5/6847; A61B 5/0538; A61B 5/14735; A61B 2562/046; B82Y 10/00; B82Y 15/00; B01L 3/502753; B01L 2400/0424; B01L 2300/0874; B01L 2400/0406; B01L 2300/0887; B01L 2300/0663; B01L 2300/0681; B01L 2300/0819
See application file for complete search history.

(56) References Cited

U.S. PATENT DOCUMENTS

| | | | |
|---|---|---|---|
| 4,777,953 A * | 10/1988 | Ash | A61B 5/14528 600/347 |
| 7,955,559 B2 * | 6/2011 | Joshi et al. | 422/68.1 |

(Continued)

OTHER PUBLICATIONS

Satija et al., Dendrimers in biosensors: Concept and applications, J. Mater. Chem., 2011, 21, 14367-14386.*

*Primary Examiner* — Tiffany Weston
*Assistant Examiner* — Tho Tran
(74) *Attorney, Agent, or Firm* — Oblon, McClelland, Maier & Neustadt, L.L.P.

(57) ABSTRACT

A biosensor includes a microfluidics layer, a transduction layer and a transceiver layer. The transduction layer further includes a functionalized layer that reacts with a biomarker, and a plurality of carbon nanotubes adjacent the functionalized layer. The conductivity of the carbon nanotubes changes in response to a biomarker reacting with at least a portion of the functionalized layer. The functionalized layer can include dendrimers, such as a tadpole dendrimer scaffolding that includes a plurality of sites for receiving receptors for biomarkers.

18 Claims, 6 Drawing Sheets

(51) Int. Cl.
    *B82Y 10/00* (2011.01)
    *H01L 51/00* (2006.01)

(52) U.S. Cl.
    CPC . *A61B 2562/0285* (2013.01); *A61B 2562/046* (2013.01); *B01L 2300/0663* (2013.01); *B01L 2300/0681* (2013.01); *B01L 2300/0819* (2013.01); *B01L 2300/0874* (2013.01); *B01L 2300/0887* (2013.01); *B01L 2400/0406* (2013.01); *B01L 2400/0424* (2013.01); *H01L 51/0049* (2013.01)

(56) References Cited

U.S. PATENT DOCUMENTS

| | | | | |
|---|---|---|---|---|
| 2004/0112529 | A1* | 6/2004 | Karlsson | B01J 19/0093 156/306.6 |
| 2004/0224002 | A1* | 11/2004 | Fishman | A61N 1/0543 424/423 |
| 2005/0137480 | A1* | 6/2005 | Alt | A61B 5/0031 600/508 |
| 2005/0201660 | A1* | 9/2005 | Grot | B82Y 20/00 385/12 |
| 2006/0258761 | A1* | 11/2006 | Boock | A61B 5/14532 521/50 |
| 2007/0007133 | A1* | 1/2007 | Mang | A61B 5/14532 204/403.14 |
| 2007/0132043 | A1* | 6/2007 | Bradley | B82Y 10/00 257/414 |
| 2007/0208243 | A1* | 9/2007 | Gabriel et al. | 600/347 |
| 2009/0139931 | A1* | 6/2009 | Leonard | A61M 1/14 210/645 |
| 2010/0165784 | A1* | 7/2010 | Jovanovich | B01F 11/0045 366/163.2 |
| 2010/0272076 | A1* | 10/2010 | Cavalcanti | H04W 74/004 370/336 |

* cited by examiner

THREE DIMENSIONAL MICROFLUIDIC MULTIPLEXED DIAGNOSTIC SYSTEM

RELATED APPLICATION

This application claims the benefit of U.S. Provisional Patent Application Ser. No. 61/507,412, filed on Jul. 13, 2011, which is incorporated by reference herein.

TECHNICAL FIELD

Various embodiments described herein relate to a three dimensional microfluidic multiplexed diagnostic system and a method for using the same.

BACKGROUND

There are certain biomarkers in the body that are associated with life altering diseases such as cancer and the like. In many instances, early treatment of such life threatening diseases give the patient much increased odds of beating such a disease. It follows that early detection of such a life threatening disease is critical.

Currently, the detection of biomarkers associated with disease has been measured in blood serum and other body fluids via assays in a diagnostic laboratory setting. The patient has to make an appointment at a lab or doctors office and to have bodily fluid drawn. The bodily fluid is then tested to determine if the biomarkers are present. These tests are typically administered to patients of selected ages or selected risk categories identified in studies or as indicated by patient or family medical history. There is no way to detect when the biomarkers may first present themselves other than a doctor "getting lucky" with the timing of a test. In many instances, a life threatening disease may have progressed well beyond the initial stages by the time a patient is tested. This can even happen in a good patient that follows the recommendations of medical professionals. Of course, if a person should fall outside of one of the identified risk categories, the disease may progress to a very late stage before the disease is diagnosed or detected. Many patients also procrastinate and hold off on getting a needed test even though they may have been identified by a medical professional as being in a high risk group for testing. In many cases, a life threatening disease advances well beyond its initial stages.

Radiological medical diagnostics, such as Computed Tomography and Positron Emission Tomography, are also used to detect life threatening diseases. However, the radiological diagnostics also fail to detect a high percentage of tumors in certain parts of the body. For example, these radiological diagnostics have difficulty in finding tumors in the pelvic cavity, as is the case for Ovarian Cancer, due to high "clutter levels", extremely small signatures and human error. Simply put, a radiologist studying the results of a radiological diagnostic test can easily miss a life threatening disease in its early stages. Typically, the patient waits for another period before radiological retesting. The disease may not be in the early stages of development by the time the life threatening disease is actually detected using radiological diagnostic tools.

SUMMARY

This 3D biosensor device will allow for early detection of biomarkers for diseases within the animal/human body. A biosensor includes a microfluidics layer, a transduction layer and a transceiver layer. A microcontroller controls input ports for gathering a sample of the fluid to be tested. An input port is opened and fluid is filtered and concentrated. The filtered and concentrated fluid is output to the transduction layer which includes a portion capable of detecting the presence of a biomarker. When a biomarker is detected, a signal is generated and sent to the transceiver layer. The transceiver layer includes an interface that allows the information to be communicated by the biosensor to receivers communicatively coupled to the biosensor.

DETAILED DESCRIPTION

Figure 1:
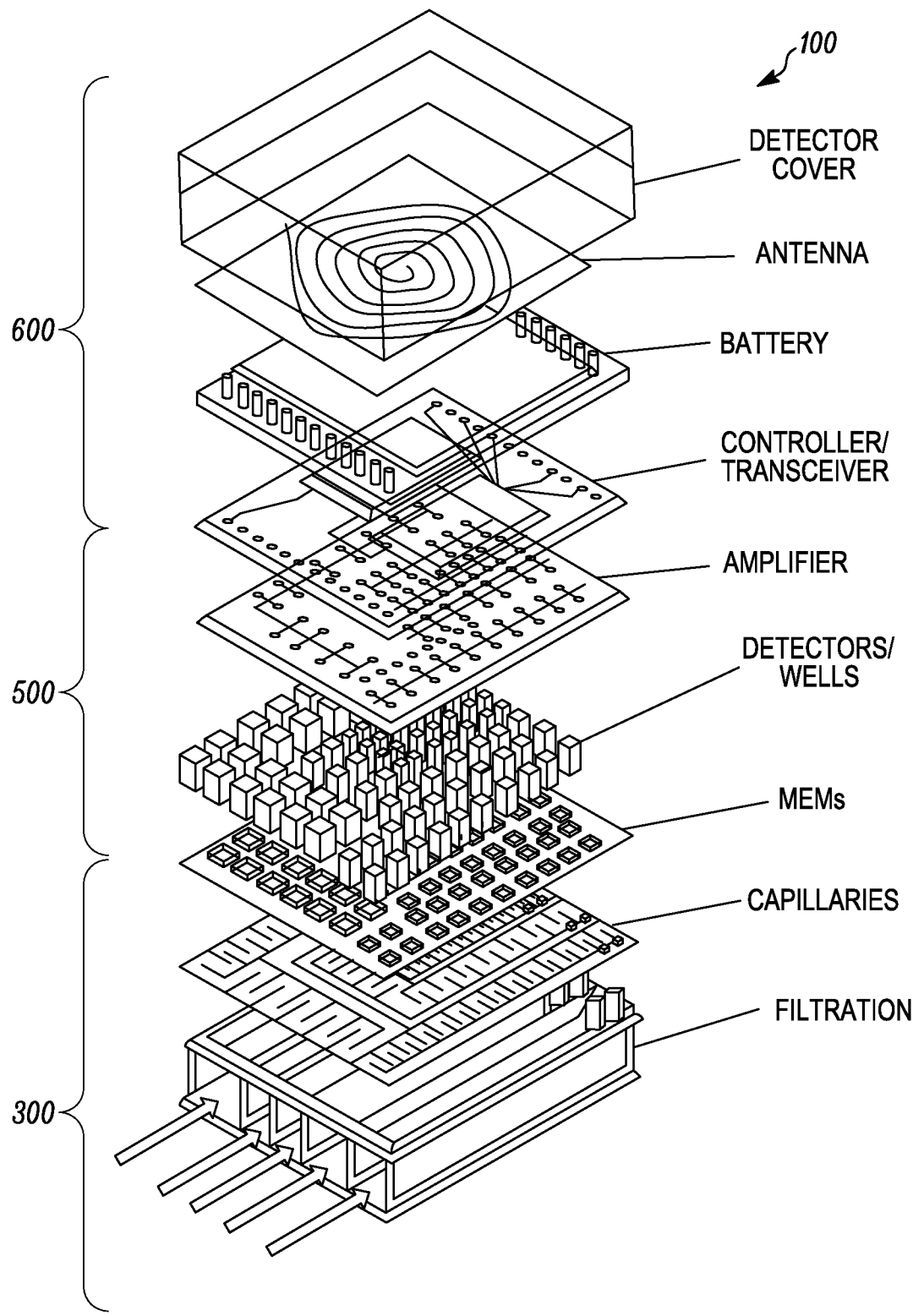
FIG. 1 is a schematic view of a three dimensional biosensor, according to an example embodiment.

FIG. 1 is a schematic view of a three dimensional biosensor 100, according to an example embodiment. The three dimensional biosensor 100 includes multiple layers. The multiple layers include a microfluidics layer 300, a transduction layer 500, and a transceiver layer 600. The three dimensional biosensor 100 is small enough so that it can be easily placed into the body. The transceiver layer 600 includes a master controller or other microprocessor 801 (seen in FIG. 6) that carries an instruction set to control other portions of the three dimensional biosensor 100. For example, the master controller or microprocessor 801 controls sampling times and locations by controlling certain aspects the of the microfluidics layer 300. The instruction set also includes instructions for operating or controlling communications with the biosensor 100 between the transceiver layer 400 and the outside world, for example.

Figure 2:
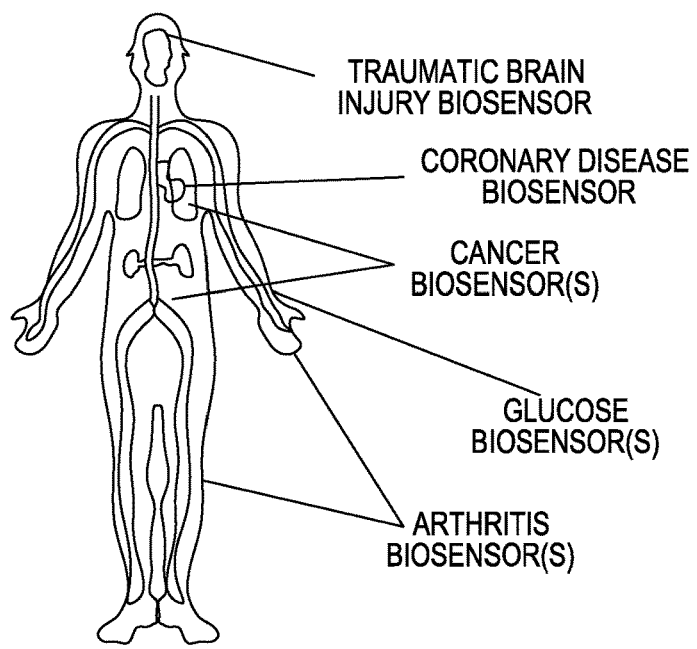
FIG. 2 shows places in a human body where the three dimensional biosensor could be used or implanted, according to an example embodiment.

FIG. 2 shows places in a human body 200 where the three dimensional biosensor 100 could be used or implanted, according to an example embodiment. The biosensor 100 could be adapted to be a cancer biosensor for detecting oncological biomarkers, an arthritis biosensor for detecting arthritic biomarkers, a glucose biosensor for monitoring diabetic biomarkers, a coronary disease biosensor for detecting biomarkers associated with coronary heart disease, or a brain injury biosensor for detecting biomarkers associated with brain injuries. Of course, it is contemplated that the biosensor could also be adapted for use to detect other biomarkers associated with other conditions. In addition, the biosensor 100 is not limited to human use, but could also be adapted for use in other animals or biological beings. In one embodiment, the three dimensional biosensor 100 can be picked up with forceps. Delivery or implantation of such a biosensor 100 is eased due to the size. Of course, it is contemplated that the biosensor 100 could be made in a smaller or larger form factor as needed. The biosensor could be inserted into the blood stream for many applications. The biosensor could also be placed into the body in a noninvasive manner, in some applications. For example, to detect or monitor for biomarkers associated with ovarian cancer, the biosensor can be delivered using an intrauterine device (IUD). As can be seen from above, the biosensor 100 is adaptable to be used in many applications and is capable of detecting many types of biomarkers. The biosensor 100 is modular which allows for flexible manufacturing. The biosensor 100 also uses the concept of bio-additive manufacturing. A rapid deposition of certain materials on one of the layers, namely the transduction layer 500, allows the biosensor to be adapted to detect different biomarkers.

Figure 3:
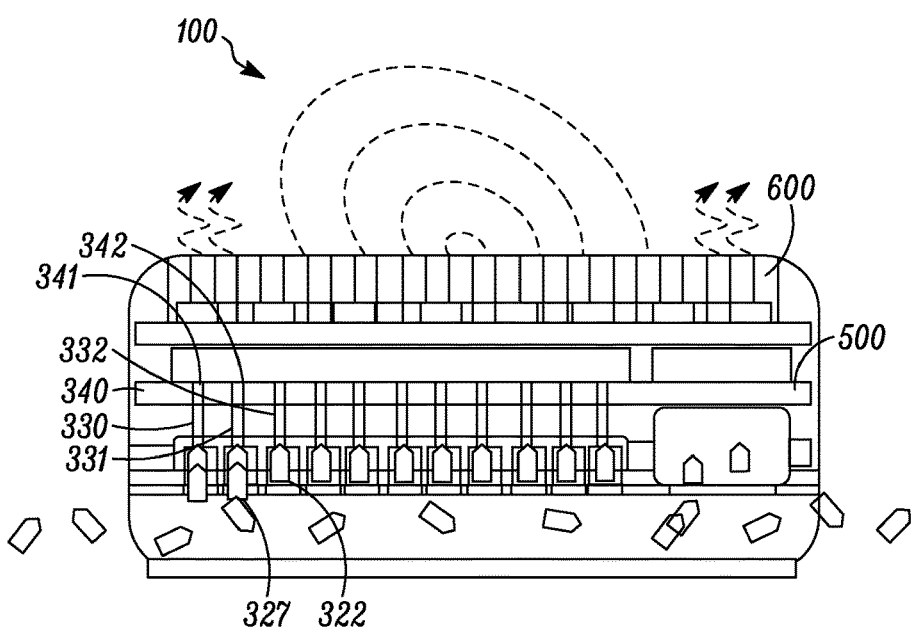
FIG. 3 is a more detailed schematic view of a three dimensional biosensor 100, according to an example embodiment.

FIG. 3 is a more detailed schematic view of a three dimensional biosensor 100, according to an example embodiment. Again, the biosensor 100 includes three layers, namely the microfluidics layer 300, the transduction layer 500, and the transceiver layer 600. The microfluidics layer 300 includes a collection portion. The body fluid to be tested flows through the collection portion. The microfluidics layer 300 also includes a plurality of input portals, including input portals 320, 321, 322 (which can be seen more clearly in FIG. 4). The input portals 320, 321, 322 control the collection of test sample material, such as the body fluid to be collected. The input portals 320, 321, 322 are connected to microfluidic filtration tunnels, such as 330, 331, 332. The filtration tunnels isolate the particles of interest from clutter in the fluidic sample. The input portals 320, 321, 322 are controlled by the master controller microprocessor 801 associated with the transceiver layer 600. In operation, the master controller microprocessor 801 opens selective input portals at a time, based on the particle of interest to be detected. The start of the testing or monitoring cycle is also controlled by the master controller microprocessor 801. The monitoring cycle is also part of the instruction set executed by the master controller the microprocessor 801. When an input portal 320, 321, 322 is opened, the corresponding microfluidic filtration tunnel such as 330, 331, 332, is exposed. The microfluidic filtration tunnels draw-in the test sample from the external environment through the opened input portals 320, 321, 322 and filter out the particle of interest via techniques such a dielectrophoresis. The particles of interest navigate to a layer of serpentine capillary distribution system, such as 330', 331', 332', where they are collected and concentrated (which can be seen more clearly in FIG. 4.). A matrix of Micro-mechanical-electronic systems (MEMs), 340, 341, 342, are used to control particle introduction into the transduction layer 500. The microfluidic module functions, namely the timing and opening of input portals and output portals, are controlled by the master controller unit or microprocessor 801, located on the transceiver layer 600. In one example embodiment, one input portal 320, 321, 322 is opened per testing or monitoring cycle. The start of the testing or monitoring cycle is also controlled by the master controller microprocessor 801. The monitoring cycle is also part of the instruction set executed by the master controller the microprocessor 801. When an input portal 320, 321, 322 is opened, the corresponding microfluidic capillary, such as one of the microfluidic capillaries 330, 331, 332, is exposed. The microfluidic capillaries draw-in the test sample from the external environment from the fluid collection area, through the opened input portal 320, 321, 322. The microfluidic capillaries include a network of micro-mechanical-electronic systems (MEMS) that separate, filter, and concentrate the target sample material. After separating, filtering, and concentrating the target sample material, the resultant fluid is passed through an output portal, such as output portals 340, 341, 342. The output portals 340, 341, 342, interface to the transduction layer 500. The microfluidic module functions, namely the timing and opening of input portals and output portals, are controlled by the master controller unit or microprocessor 801, located on the transceiver layer 600. In one example embodiment, the control signals are distributed to the three dimensional biosensor 100 using a microscale transmission structure that is distributed across all layers. A similar distribution network is used to provide DC power to the active components. In some embodiments, the power is generated through movement of the hosts' muscles so as to lessen or eliminate the need for batteries or the like. It should be noted, that once a sample is taken, the biosensor 100 holds the sample as opposed to flushing the input portal, the output portal and the microfluidic channels. The filtered, concentrated, and otherwise treated fluid may be a contaminant to the body in which the biosensor 100 is operating. Therefore, the fluid is held and once the input portal is opened, it exposes the corresponding microfluidic channels to the fluid for a one time use. The output portal is also used one time as is a portion of the transduction layer 500. Thus the biosensor 100 has a limited life since each time a test is run, the portion of the biosensor 100 used cannot be used again.

Figure 4:
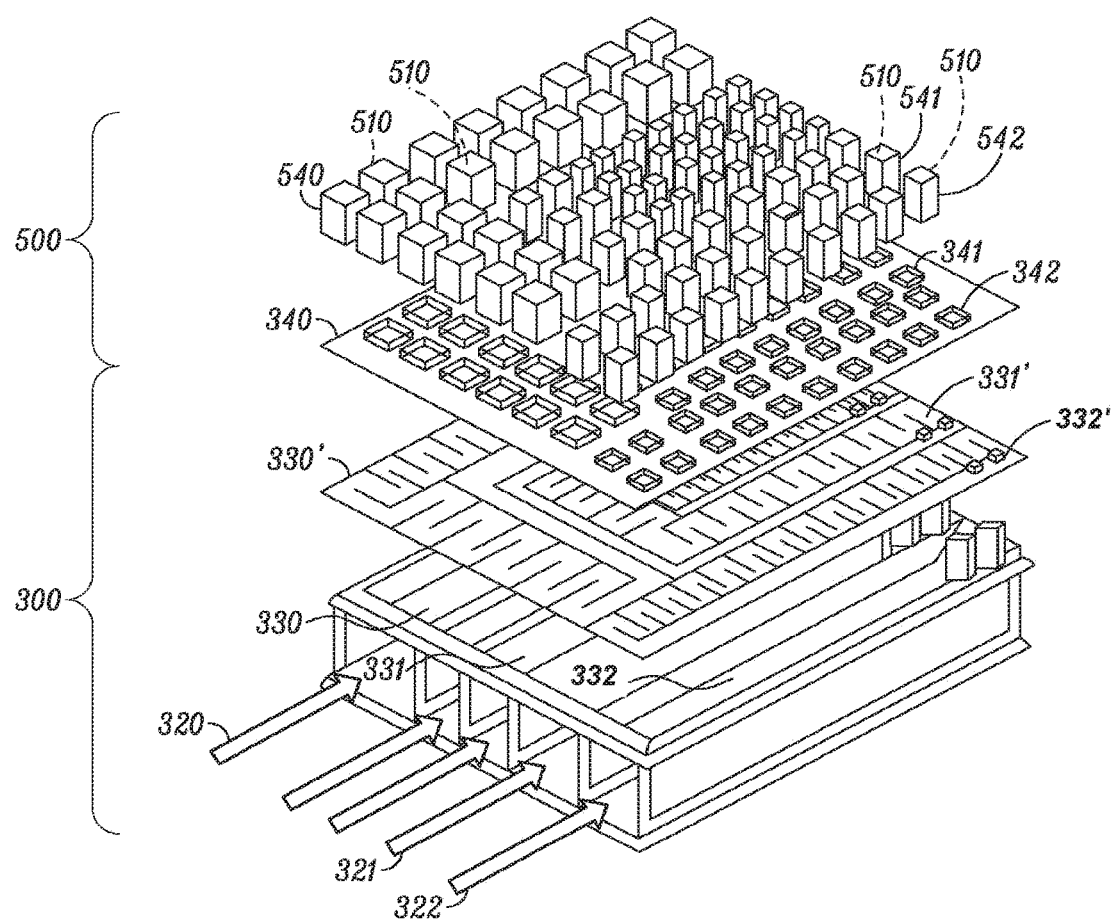
FIG. 4 is a schematic view of the input portals, the microfluidics channels associated therewith, the output portals, and portions of the transduction layer associated or interfacing with corresponding to output portals from the microfluidics layer, according to an example embodiment.

FIG. 4 is a schematic view of the input portals 320, 321, 322, the microfluidic filtration tunnels associated therewith 330, 331, 332, the serpentine capillaries for particle distribution 330', 331', 332', the MEMs-based output portals 340, 341, 342, and portions 540, 541, 542 of the transduction layer 500 associated or interfacing with corresponding output portals 340, 341, 342, from the microfluidics layer 300, according to an example embodiment. The transduction layer 500 includes a number of locations 540, 541, 542 where the separated, filtered, and concentrated target sample material is delivered. In one embodiment, there are a multiplicity of such positions. When an output portal, such as output portal 340 is opened, the separated, filtered, and concentrated target sample material is delivered to the location 540. Once the separated, filtered, and concentrated target sample material is delivered to a location, that location cannot be used again. Each location contains a detector surface 510, which can be functionalized with different types of DNA, peptides, or antibodies that will react with different biomarkers in the target sample fluid (which can be seen more clearly in FIG. 5). Generally, it is desirable to detect the least number of biomarkers since this will require the least amount of space on the transduction layer 500. Testing or detecting fewer biomarkers means less space needs to be dedicated to a single location. Less real estate on a location means that more locations can be packed onto a transduction layer 500 and the resulting biosensor 100 will be good for more testing cycles and have a longer life. When a biomarker attaches to a DNA, peptides or antibody at surface 510, the electric conductivity of the surface changes which indicates that a biomarker is present in the sample fluid. The conductivity of surface 510 is monitored. The surface 510 is wired for such monitoring and any change in conductivity is communicatively coupled to the transceiver layer 600, or more specifically to the controller or microprocessor 801 in the transceiver layer 600 where the information is communicated outside the biosensor 100.

The transduction layer 500 consists of a matrix of locations, such as 540, 541 and 542, functionalized with a transduction surface 510. The surface 510 is provided with a surface which can be functionalized with various biomarker detectors. Certain biomarkers will react with DNA, peptides, or antibodies. The surface 510 is functionalized by adding or populating the surface 510 with the DNA, peptides, or antibodies. As mentioned previously, the biosensor 100 uses the concept of bio-additive manufacturing. DNA, peptides, or antibodies are placed on the surface 510 by way of a rapid deposition of the materials (DNA, peptides, or antibodies) used to detect biomarkers. It should be noted that specific DNA, peptides or antibodies react with specific biomarkers to be sensed. The biosensor 100 is flexible since the rapid deposition of materials is all that is needed to change the application of the biosensor 100 from one for detecting cancer to one that detects arthritis. To form the different biosensor, the surface 510 is populated with different DNA, peptides, or antibodies that are needed to detect the different set of biomarkers. The specific biomarker attaches to the DNA, peptides or antibody on the surface 510. Sometimes the DNA, peptides, or antibody when combined with the biomarker, stays attached to the layer 510 and at other times the combination tears away. In either instance, the conductivity of the surface at the functionalized site changes indicating the presence of the biomarker.

In summary, the transduction layer 500 is where the chemical signature for a biomarker in the filtered and concentrated sample fluid is converted to an electronic signature. The transduction surface, such as functionalized surface locations 540, 541, 542 that interfaces to the microfluidics layer 300.

Figure 5:
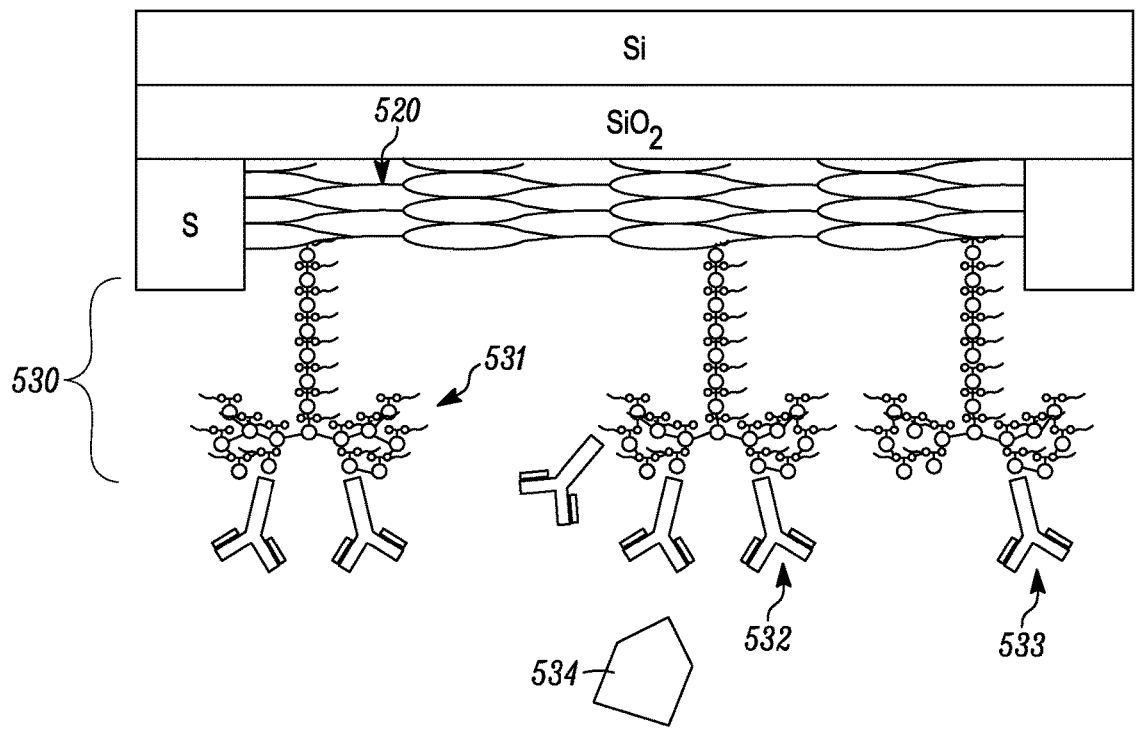
FIG. 5 is a schematic cross sectional view of the surface of the transduction layer within the biosensor, according to an example embodiment.

FIG. 5 is a schematic cross sectional view of the surface 510 (FIG. 4) of the transduction layer 500 within the biosensor 100, according to an example embodiment. The detailed view of surface 510 shown in FIG. 5 is functionalized which means that the antigens, peptides or DNA that reacts with the biomarkers to be detected has been placed on the surface 510. In one embodiment, the surface 510 includes carbon nanotube based field-effect biosensors (BIOFET) 520 and a layer of dendrimers 530. The carbon nanotube BIOFETs 520 are very sensitive to many environmental changes. For example, changes in humidity change the measurable properties of the carbon nanotubes in the carbon nanotube layer 520. The layer of dendrimers 530 isolate the carbon nanotubes from these environmental changes. The dendrimers 530, therefore, stabilize the properties of the carbon nanotubes. The carbon nanotubes remain sensitive and, for example, can detect small changes in the conductivity of the dendrimer layer 530. Individual dendrimers, such as tadpole dendrimer 531, are functionalized by attaching antibodies, antigens or DNA that reacts with a biomarker of interest to the tadpole dendrimer 531. More specifically, the functionalized surface chemistry is deposited onto the top surface dendrimer branching networks. It should be noted that having access to the dendrimer branching structures on the transduction surface 510, enables flexible manufacture of the functionalized surface biologics supporting maximum design reuse.

The antibody, antigen or DNA provides a receptor 532, 533 to which a biomarker of interest will or can attach. The receptor 532, 533 will not react with other bioelements. However, when a biomarker of interest is present in the concentrated, filtered fluid sample, it attaches to the receptor 532, 533. As shown in FIG. 5, a biomarker 534 is attached to the receptor 532. This changes the electrical conductivity of the dendrimer 531 which is, in turn, detected by the carbon nanotubes of carbon nanotube layer 520.

In operation, the target analyte or biomarker contained within the fluid sample is flowed across the functionalized surface chemistry of layer 530 where the dendrimer nanostructure forest is changed by the surface chemical reaction with the captured analyte. The surface state changes are transferred to the carbon nanotube mat 520 eliciting a change in conductivity between a source electrode and drain electrodes. The structure can be compared to a CMOS transistor. The transduction layer 500 is a highly integrated array of detection elements or positions 540 integrated into tiles or subpositions 540'. The subpositions or tiles can also be termed as detector wells that are configured as subarrays supporting relative measurement capability. The detection array enables specific subarray clusters to be exposed to the test samples enabling periodic testing of the external in vivo environment, using a small section of the array surface for each test cycle. The electronic signals from the transducer layer are processed by the digital electronics on the transceiver layer 600, modulated and transmitted via the surface mount antenna 610 located on the transceiver layer.

Figure 6:
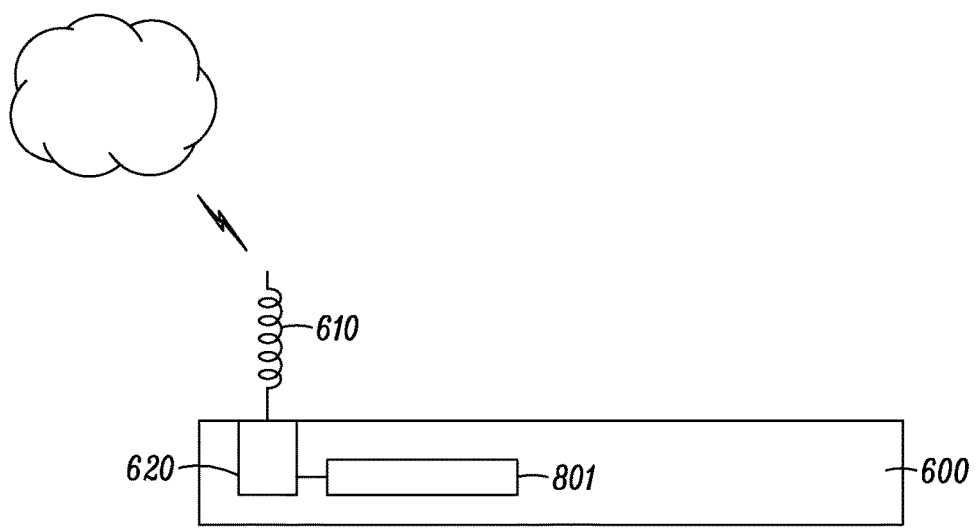
FIG. 6 is a schematic top view of the transceiver layer within the biosensor, according to an example embodiment.

FIG. 6 is a schematic view of the transceiver layer 600, according to an example embodiment. The transceiver layer 600 includes an antenna 610 for communications between the biosensor 100 and other devices. The transceiver layer 600 includes a transceiver 620 for incoming and outgoing communication of information. The transceiver 620 also receives and processes electronic signals from the transduction layer 500. In one example embodiment, the electronic signals from the transduction layer 500 are processed by the digital electronics on the transceiver layer, modulated and transmitted via the surface mount antenna 610 located on the top of the transceiver layer 600. One example embodiment includes multi-scale transposer vertical interconnect vias that provide RF isolation and which transmit RF transmissions. In one embodiment, the transceiver 620 and the master controller 801 can be configured as a computer capable of communicating via a wi-fi network or other network. If the biosensor 100 detects a biomarker for example, the microprocessor or master controller 801 can be instructed to communicate the result to the patient's doctor's office. Instructions, in some embodiments, can be received via wi-fi or other network to reprogram the biosensor 100.

Figure 7:
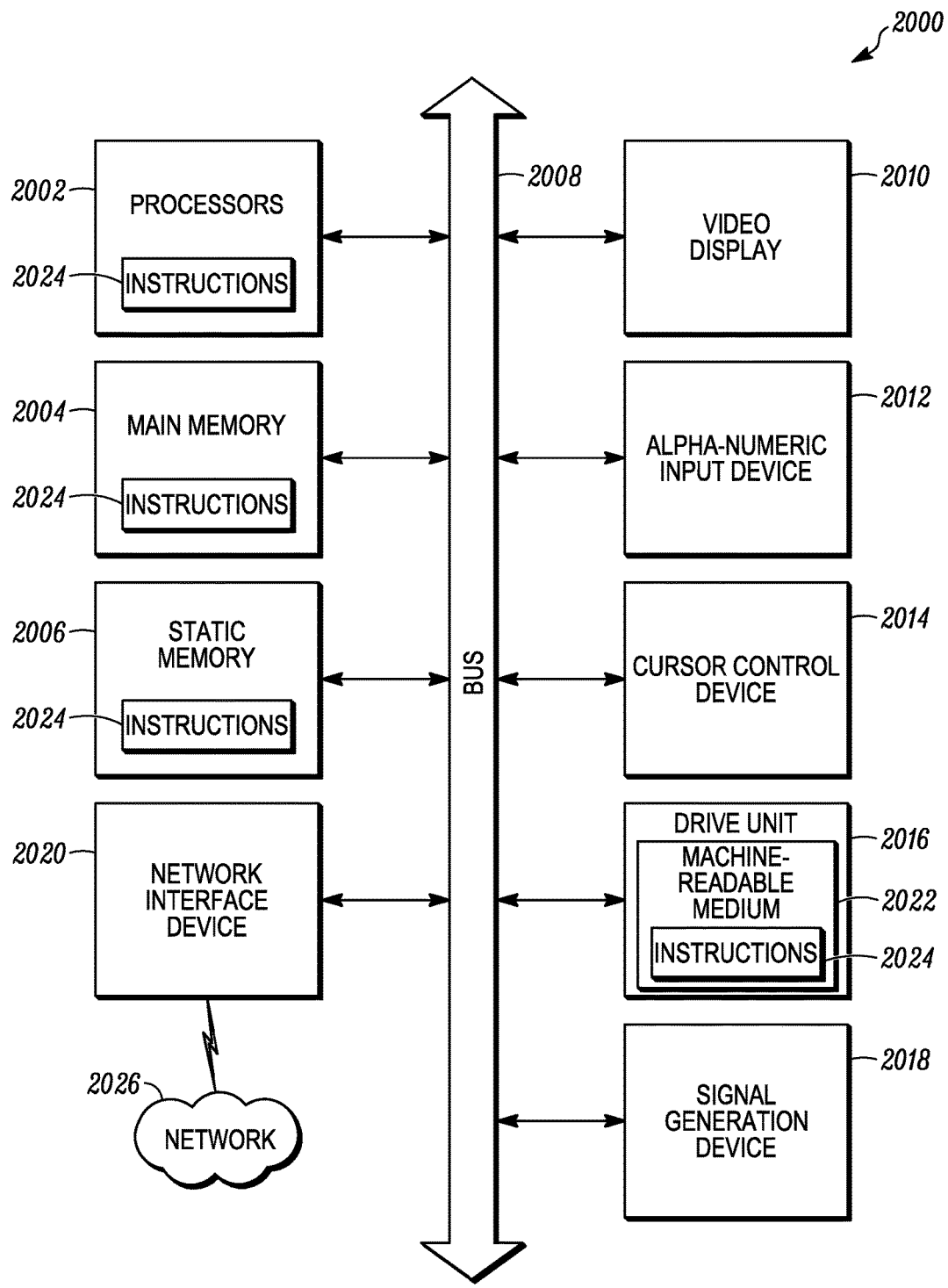
FIG. 7 is a schematic view of a computer, such as the master controller found in the transceiver layer, according to an example embodiment.

FIG. 7 is a schematic view of a computer 2000, such as the master controller 801 found in the transceiver layer 600, according to an example embodiment. FIG. 7 shows a diagrammatic representation of a computing device for a machine in the example electronic form of a computer system 2000, within which a set of instructions for causing the machine to perform any one or more of the methodologies discussed herein can be executed or is adapted to include the apparatus for detection of biomarkers as described herein. In various example embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a Personal Digital Assistant (PDA), a cellular telephone, a portable music player (e.g., a portable hard drive audio device such as an Moving Picture Experts Group Audio Layer 3 (MP3) player, a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2000 includes a processor or multiple processors 2002 (e.g., a central processing unit (CPU), a graphics processing unit (GPU), arithmetic logic unit or all), and a main memory 2004 and a static memory 2006, which communicate with each other via a bus 2008. The computer system 2000 can further include a video display unit 2010 (e.g., a liquid crystal displays (LCD) or a cathode ray tube (CRT)). The computer system 2000 also includes an alphanumeric input device 2012 (e.g., a keyboard), a cursor control device 2014 (e.g., a mouse), a disk drive unit 2016, a signal generation device 2018 (e.g., a speaker) and a network interface device 2020.

The disk drive unit 2016 includes a computer-readable medium 2022 on which is stored one or more sets of instructions and data structures (e.g., instructions 2024) embodying or utilized by any one or more of the methodologies or functions described herein. The instructions 2024 can also reside, completely or at least partially, within the main memory 2004 and/or within the processors 2002 during execution thereof by the computer system 2000. The main memory 2004 and the processors 2002 also constitute machine-readable media.

The instructions 2024 can further be transmitted or received over a network 2026 via the network interface device 2020 utilizing any one of a number of well-known transfer protocols (e.g., Hyper Text Transfer Protocol (HTTP/HTTPS), File Transfer Protocol (FTP/FTPS), CAN, Serial, or Modbus).

While the computer-readable medium 2022 is shown in an example embodiment to be a single medium, the term "computer-readable medium" should be taken to include a single medium or multiple media (e.g., a centralized or distributed database, and/or associated caches and servers) that store the one or more sets of instructions and provide the instructions in a computer readable form. The term "computer-readable medium" shall also be taken to include any medium that is capable of storing, encoding, or carrying a set of instructions for execution by the machine, that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, tangible forms and signals that can be read or sensed by a computer. Such media can also include, without limitation, hard disks, floppy disks, flash memory cards, digital video disks, random access memory (RAMs), read only memory (ROMs), and the like.

Figure 8:
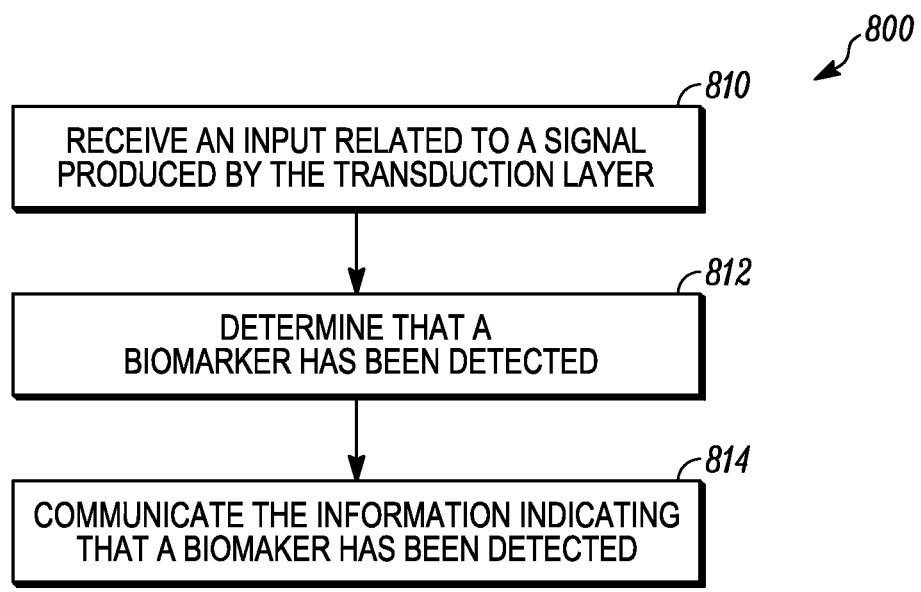
FIG. 8 is a schematic cross sectional view of the transceiver layer, according to an example embodiment.

FIG. 8 is a flow diagram associated with a computerized method 800, according to an example embodiment. The computerized method includes receiving an input related to a signal produced by the transduction layer 810, determining that a biomarker has been detected 812, and communicating the information indicating that a biomarker has been detected 814. When the computerized method 800, discussed above, is programmed into a memory of a general purpose computer, the computer and instructions form a special purpose machine. The instructions, when programmed into a memory of a general purpose computer, is in the form of a non transitory set of instructions. Additional instructions discussed above also transform the computer into a specialized machine associated with the biosensor 100. The additional instructions are also non transitory.

The example embodiments described herein can be implemented in an operating environment comprising computer-executable instructions (e.g., software) installed on a computer, in hardware, or in a combination of software and hardware. Modules as used herein can be hardware or hardware including circuitry to execute instructions. The computer-executable instructions can be written in a computer programming language or can be embodied in firmware logic. If written in a programming language conforming to a recognized standard, such instructions can be executed on a variety of hardware platforms and for interfaces to a variety of operating systems making it platform independent. Although not limited thereto, computer software programs for implementing the present method(s) can be written in any number of suitable programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Java™, Jini™, C, C++, Perl, UNIX Shell, Visual Basic or Visual Basic Script, Virtual Reality Markup Language (VRML), ColdFusion™ or other compilers, assemblers, interpreters or other high or low level computer languages or platforms.

The present disclosure refers to instructions that are received at a memory system. Instructions can include an operational command, e.g., read, write, erase, refresh, etc., an address at which an operational command should be performed, and the data, if any, associated with a command. The instructions can also include error correction data.

A biosensor includes a microfluidics layer, a transduction layer, and a transceiver layer. The transduction layer further includes a functionalized layer that reacts with a biomarker, and a plurality of carbon nanotubes adjacent the functionalized layer. The conductivity of the carbon nanotubes changes in response to a biomarker reacting with at least a portion of the functionalized layer. The functionalized layer can include dendrimers, such as a tadpole dendrimer scaffolding that includes a plurality of sites for receiving receptors for biomarkers. In one embodiment, the carbon nanotubes are field-effect biosensors (BIOFET). This above described tadpole dendrimer scaffolding structure isolates the carbon nanotube BIOFET from exposure to external contaminants to help ensuring maximum sensitivity to the target analyte.

In one embodiment, the functionalized layer includes a plurality of one time use test locations. The biosensor also includes a conductivity monitor which monitors conductivity of the functionalized layer and the carbon nanotube layer for changes in conductivity. The conductivity monitor is communicatively coupled to the transceiver layer. The e microfluidics layer of the biosensor can include a plurality of capillaries through which a test samples of fluids flow. A plurality of input portals in are fluid communication with a plurality of capillariesa through which a test samples of fluids flow. The biosensor also includes a plurality of output portals in fluid communication with a plurality of capillaries. The output portals place fluid samples on portions of the functionalized layer of the transduction layer. The opening and closing of the input portals and the output portals is controllable by a processor in the transceiver layer. The transceiver layer of the biosensor includes a processor for controlling portions of the microfluidics layer and monitoring the conductivity of portions of the transduction layer and for controlling communications with the biosensor.

A biosensor includes a microfluidics layer for collecting samples, a transduction layer for determining if selected biomarkers are present in a fluid sample, and a transceiver layer. The microfluidics layer deposits a sample onto a portion of the transduction layer. The transceiver layer further includes a processor for controlling the microfluidics layer and monitoring the transduction layer for an indication that a selected biomarker, and a communications device enabling communications with the biosensor. The transduction layer further includes a functionalized layer that reacts with a biomarker, and a plurality of carbon nanotubes adjacent the functionalized layer. The conductivity of the carbon nanotubes changes in response to the a biomarker reacting with at least a portion of the functionalized layer. In one embodiment, the transduction layer includes multi-scale transposer vertical interconnect vias having carbon nanotube (CNT) filler which provides RF isolation and signal transmission functionality. In still another embodiment, the carbon nanotubes act as a field-effect biosensor. The functionalized layer includes a layer of dendrimers that includes receptor sites for biomarkers. The biosensor also includes a conductivity monitor. The conductivity monitor monitors conductivity of the functionalized layer and the carbon nanotube layer for changes in conductivity and communicates an indication of change in conductivity to processor in the transceiver layer. The microfluidics layer includes a plurality of capillary tubes through which a test sample of fluid flows. The fluid flow in at least one of the capillary tubes or capillaries is controlled by the processor in the transceiver layer. The biosensor also includes a system for separating, filtering and concentrating a sample fluid, the system associated with the plurality of capillary tubes through which test samples of fluids flow. In some embodiments, the system is implemented using a MEMs device or plurality of MEMs devices. The microfluidics layer includes the plurality of capillary tubes or plurality of capillaries. A plurality of input portals and a plurality of output portals are in fluid communication with the plurality of capillaries. The output portals place fluid samples on portions of the functionalized layer of the transduction layer. In some embodiments, at least one of the capillary tubes having an input portal and an output portal controllable by the processor of the transceiver layer.

The biosensor also includes an instruction set which is executable by the processor of the biosensor. The instructions, when executed by the processor, control the fluid flow in the microfluidics layer, and monitor the transduction layer for an indication of presence of a selected biomarker, and communicate the indication of the selected biomarker from the biosensor to another device, such as another computing device in a network. The network can include any type of network including the Internet.

A method includes placing a biosensor in a body and collecting a fluid from the body with the biosensor. The collected fluid is delivered to a test site within the biosensor. The collected fluid can be filtered and concentrated on board the biosensor. The test site is monitored within the biosensor for an indication that a selected biomarker is present in the fluid. If there is a positive indication that a biomarker is present, the processor controllably communicates the indication to a device other than the biosensor, such as a networked device. In this way, a person or animal can be monitored for biomarkers and the like. If a biomarker is present, this information can be related to a health care professional and to the animal or person carrying the biosensor.

This has been a detailed description of some exemplary embodiments of the invention(s) contained within the disclosed subject matter. Such invention(s) may be referred to, individually and/or collectively, herein by the term "invention" merely for convenience and without intending to limit the scope of this application to any single invention or inventive concept if more than one is in fact disclosed. The detailed description refers to the accompanying drawings that form a part hereof and which shows by way of illustration, but not of limitation, some specific embodiments of the invention, including a preferred embodiment. These embodiments are described in sufficient detail to enable those of ordinary skill in the art to understand and implement the inventive subject matter. Other embodiments may be utilized and changes may be made without departing from the scope of the inventive subject matter. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed:

1. A biosensor adapted for implantation comprising:
   a microfluidics layer including
      microfluidic filtration tunnels configured to filter a fluid sample using dielectrophoresis,
      a matrix of micro-mechanical-electronic systems (MEMS) configured to open and close input and output portals at predetermined times, and
      microfluidic capillaries positioned between the microfluidic filtration tunnels and the matrix of MEMS, wherein the microfluidic capillaries are configured to draw in the filtered fluid sample from the microfluidic filtration tunnels, wherein the filtered fluid sample is drawn in perpendicular to a direction of fluid flow through the microfluidic filtration tunnels;
   a transceiver layer; and
   a transduction layer positioned between the microfluidics layer and the transceiver layer and interfaced to the microfluidics layer via the output portals, wherein the transduction layer is configured to detect a biomarker of the filtered fluid sample, the transduction layer comprising:
      a functionalized layer that reacts with the biomarker of the filtered fluid sample;
      a plurality of carbon nanotubes adjacent the functionalized layer, the conductivity of the plurality of carbon nanotubes changing in response to a biomarker reacting with at least a portion of the functionalized layer.

2. The biosensor adapted for implantation of claim 1 wherein the functionalized layer includes dendrimers.

3. The biosensor adapted for implantation of claim 1 wherein the functionalized layer includes a tadpole dendrimer scaffolding for receiving receptors of biomarkers.

4. The biosensor adapted for implantation of claim 1 wherein the functionalized layer includes a plurality of one time use test locations.

5. The biosensor adapted for implantation of claim 1 further including a conductivity monitor which monitors conductivity of the functionalized layer and the plurality of carbon nanotubes for changes in conductivity.

6. The biosensor adapted for implantation of claim 5 wherein the conductivity monitor is communicatively coupled to the transceiver layer.

7. The biosensor adapted for implantation of claim 1 wherein the microfluidics layer includes a plurality of capillary tubes through which fluid samples flow.

8. The biosensor adapted for implantation of claim 1 wherein the microfluidics layer includes:
a plurality of capillary tubes through which fluid samples flow;
a plurality of input portals in fluid communication with the plurality of capillary tubes through which fluid samples flow; and
a plurality of output portals in fluid communication with a plurality of capillary tubes, the output portals placing fluid samples on portions of the functionalized layer of the transduction layer.

9. The biosensor adapted for implantation of claim 8 wherein the opening and closing of the input portals is controllable by a processor in the transceiver layer.

10. The biosensor adapted for implantation of claim 1 wherein the transceiver layer includes a processor for controlling portions of the microfluidics layer and monitoring the conductivity of portions of the transduction layer and for controlling communications with the biosensor.

11. A biosensor, for sensing a biomarker, adapted for implantation comprising:
a microfluidics layer including
microfluidic filtration tunnels configured to filter a fluid sample using dielectrophoresis,
a matrix of micro-mechanical-electronic systems (MEMS) configured to open and close input and output portals at predetermined times, and
microfluidic capillaries positioned between the microfluidic filtration tunnels and the matrix of MEMS, wherein the microfluidic capillaries are configured to draw in the filtered fluid sample from the microfluidic filtration tunnels, wherein the filtered fluid sample is drawn in perpendicular to a direction of fluid flow through the microfluidic filtration tunnels;
a transceiver layer comprising:
processing circuitry configured to
control the microfluidics layer, and
monitor the transduction layer for an indication that the predetermined biomarker is present; and
a communications device enabling communications between the biosensor and one or more external devices via a network; and
a transduction layer positioned between the microfluidics layer and the transceiver layer and interfaced to the microfluidics layer via the output portals, wherein the transduction layer is configured to detect a biomarker of the filtered fluid sample, the transduction layer comprising:
a functionalized layer that reacts with the biomarker of the filtered fluid sample; and
a plurality of carbon nanotubes adjacent the functionalized layer, the conductivity of the plurality of carbon nanotubes changing in response to a biomarker reacting with at least a portion of the functionalized layer.

12. The biosensor adapted for implantation of claim 11 wherein the transduction layer further comprises:
a functionalized layer that reacts with the predetermined biomarker; and
a plurality of carbon nanotubes adjacent the functionalized layer, the conductivity of the plurality of carbon nanotubes changing in response to the predetermined biomarker reacting with at least a portion of the functionalized layer, the plurality of carbon nanotubes acting as a field-effect biosensor.

13. The biosensor adapted for implantation of claim 12 wherein the functionalized layer includes a layer of dendrimers that includes receptor sites for the predetermined biomarkers.

14. The biosensor adapted for implantation of claim 12 further including a conductivity monitor which monitors conductivity of the functionalized layer and the plurality of carbon nanotubes for changes in conductivity and sends an indication of change in conductivity to the processor in the transceiver layer.

15. The biosensor adapted for implantation of claim 12 wherein the microfluidics layer includes a plurality of capillary tubes through which fluid samples flow, the fluid flow in at least one of the capillary tubes controlled by the processor in the transceiver layer.

16. The biosensor adapted for implantation of claim 11 wherein the microfluidics layer includes:
a plurality of capillary tubes through which fluid samples flow;
a plurality of input portals in fluid communication with a plurality of capillary tubes through which fluid samples flow; and
a plurality of output portals in fluid communication with a plurality of capillary tubes, the output portals placing fluid samples on portions of the functionalized layer of the transduction layer, at least one of the capillary tubes having an input portal and an output portal controllable by the processor of the transceiver layer.

17. The biosensor adapted for implantation of claim 11 wherein the processor includes an instruction set executable by the processor, the instructions for
controlling the fluid flow in the microfluidics layer;
monitoring the transduction layer for an indication of presence of a predetermined biomarker; and
communicating the indication of the predetermined biomarker from the biosensor to another device.

18. A method comprising:
implanting a biosensor in a body, the biosensor including a microfluidics layer, the microfluidics layer including microfluidic filtration tunnels configured to filter a fluid sample using dielectrophoresis,
a matrix of micro-mechanical-electronic systems (MEMS) configured to open and close input and output portals at predetermined times, and
microfluidic capillaries positioned between the microfluidic filtration tunnels and the matrix of MEMS, wherein the microfluidic capillaries are configured to draw in the filtered fluid sample from the microfluidic filtration tunnels, wherein the filtered fluid sample is drawn in perpendicular to a direction of fluid flow through the microfluidic filtration tunnels;
delivering the fluid to a test site within the biosensor, wherein the test site includes a transduction layer positioned above between the microfluidics layer and a transceiver layer and interfaced to the microfluidics layer via the output portals, wherein the transduction layer is configured to detect a biomarker of the filtered fluid sample;

monitoring the test site within the biosensor for an indication that the predetermined biomarker is present in the fluid; and communicating the indication to a device other than the biosensor.

* * * * *